United States Patent [19]
Lanning et al.

[11] Patent Number: 5,648,085
[45] Date of Patent: Jul. 15, 1997

[54] REDUCING PESTICIDE RESISTANCE

[75] Inventors: Christine L. Lanning, Durham; Mohammed B. Abou-Donia, Chapel Hill; Robert L. Fine; James J. Corcoran, both of Durham, all of N.C.

[73] Assignee: Duke University, Durham, N.C.

[21] Appl. No.: 403,963

[22] Filed: Mar. 15, 1995

[51] Int. Cl.$^6$ ..................... A01N 25/00

[52] U.S. Cl. ............ 424/405; 514/89; 514/65; 514/478; 514/305

[58] Field of Search ............ 514/89, 65, 478, 514/305; 546/25; 424/408

[56] References Cited

U.S. PATENT DOCUMENTS

| | | | |
|---|---|---|---|
| 4,812,449 | 3/1989 | Rideout | 514/183 |
| 4,888,325 | 12/1989 | Schroeder et al. | 514/25 |
| 5,192,546 | 3/1993 | Abercrombie | 424/405 |
| 5,306,628 | 4/1994 | Sivasubramanian et al. | 435/69.7 |
| 5,364,843 | 11/1994 | King | 514/15 |
| 5,369,009 | 11/1994 | Arceci et al. | 435/7.23 |

OTHER PUBLICATIONS

"Disruption Of The Mouse mdr1a P-Glycoprotein Gene Leads To A Deficiency In The Blood-Brain Barrier And To Increased Sensitivity To Drugs", A.H. Schinkel et al., *Cell*, vol. 77, pp. 491-502, May 20, 1994, Copyright ©1994 by Cell Press.

"Insect Resistance To Insecticides: Mechanisms And Diagnosis", N.R. Price, *Comp. Biochem. Physiol.*, vol. 100C, No. 3, pp. 319-326, 1991.

Albert Selective Toxicity pp. 3, 13 1973.

Sarkadi et al.; Expression Of Human Multidrug Resistance—in J. Biological Chemistry vol. 267 #7 Mar. 5, 1992 pp. 4854-4858.

Somani et al Drug Interaction for Plasma Protein Binding— in J. Clin. Pharm. Therapy & Toxicology vol. 25 #8—1987 pp. 412-416.

*Primary Examiner*—Neil S. Levy
*Attorney, Agent, or Firm*—Banner & Witcoff, Ltd.

[57] ABSTRACT

Pest populations that have developed pesticide resistance can be treated and killed with an inhibitor for ATP-dependent 150-180 kDa membrane P-glycoprotein as a pretreatment or simultaneously with application of a pesticide at doses which, by themselves, are not toxic to the pests.

21 Claims, No Drawings

REDUCING PESTICIDE RESISTANCE

FIELD OF THE INVENTION

The invention relates to pesticide formulations that inhibits pesticidal resistance in target pests.

BACKGROUND OF THE INVENTION

The development of pesticide resistance is a major problem in the control of many types of pests. To date, more than 500 species (including rats, mice, German cockroaches, mosquitoes, *Drosphilia melanogaster*, and tobacco budworms) are known to have developed resistance to the toxic effects of a variety of pesticides. Pesticide resistance is characterized by multiple mechanisms including increased detoxification, reduced absorption of applied pesticides, increased tolerance of the pesticide by the target pest, and increased elimination from the pest of the applied pesticide. Such resistance interjects elements of uncertainty when applying pesticides to target pests and can require a regimen of increasing application rates or ever-changing pesticides to overcome or prevent the development of resistance.

Sivasubramanian et al. U.S. Pat. No. 5,306,628 proposes the combination of insecticidal proteins in combination with a vital polypeptide specific for the gut epithelium of the target insect for increasing the effectiveness of b. thuringiensis. Unfortunately, the specificity of the polypeptide does not lend itself to a formulation for inhibiting or overcoming an array of pesticide resistance in diverse target pest populations.

It would be useful to have a pesticide formulation that would inhibit pesticide resistance or reverse a developed resistance in an array of target pests.

SUMMARY OF THE INVENTION

It is an objective of the invention to provide a pesticide formulation that inhibits the development of pesticide resistance or reverses a developed resistance in an array of target pests.

In accordance with this and other objectives of the invention that will become apparent from the description herein, pesticide formulations according to the invention comprise: (a) an inhibitor for ATP-dependent 150–180 kDa membrane P-glycoprotein; and (b) an active pesticide in an amount sufficient to control a population of a target pest.

The 150–180 kDa membrane P-glycoprotein influences the transport of pesticides out of cells in target pests in a process that uses ATP as a source of energy. This lowers the pesticide concentration within the cell and permits the target pest to avoid mortality. When such a transport mechanism develops efficiency, the target pests is able to excrete the pesticide before toxic concentration levels can be achieved and is said to be resistant to the pesticide. With pesticide formulations according to the present invention, however, the efflux of pesticide out of the cell is blocked or disrupted. Pesticide resistance is not allowed to manifest, and most resistance that has developed is reversed.

DETAILED DESCRIPTION

Pesticide compositions according to the invention involve a combination of an inhibitor for ATP-dependent 150–180 kDa membrane P-glycoprotein and a pesticide. The inventors have determined that P-glycoprotein (P-gp) levels are increased in tissues associated with excretion of chemicals in pests exposed to various pesticides. For example, analysis of tissues from male rats that had been administered chlorpyrifos showed greatly increased levels of P-gp in large bile ducts of the liver and proximal tubules of the kidney, diffuse staining in the adrenal medulla and cortex, and moderate staining in the epithelial layers of the stomach and jejunum.

In connection with further studies showing interaction between pesticides and P-gp, the evidence supports a conclusion that P-gp plays a role in the cellular detoxification of pesticides and development of resistance to such pesticides. Resistant tobacco budworms exhibited 1.8–6.4 times the amount of P-gp compared to susceptible budworms located in the cuticle and fat body.

The effect of P-gp in the present invention resembles the multidrug resistance (MDR) phenotype encountered in human chemotherapy for cancer. In MDR, the P-gp (170 Kda) mediates MDR and functions by pumping the toxic agent out of the cell. Such a mechanism may occur in the development of pesticide resistance and which is addressed by the present invention.

The present invention is directed to a formulation of a pesticide and an inhibitor for P-gp. The P-glycoprotein inhibitor interferes, on a cellular level, with the pest's biological ability to flush the pesticide from its cells and avoid developing a toxic concentration of pesticide. By either adding an inhibitor for P-gp and combining the two materials in a single pesticidal product or by pretreating the target pest population with the inhibitor component before contact with the pesticide, the efficacy of the pesticide is maintained or reinstated.

Suitable P-glycoprotein inhibitors used in compositions according to the present invention are not generally recognized as effective as pesticides. Suitable inhibitors include calcium channel blockers (e.g., verapamil, azidopine, nicardipine, nimodipine), calmodulin antagonists, steroid agonists or antagonists (e.g., tamoxifen), quinine, quinidine, protein kinase C inhibitors (e.g., sphingosine), cyclosporins and analogues thereof, and naturally-occurring materials containing one or more of these inhibitors.

When used as a combination product, the P-glycoprotein inhibitor is added to the composition in an amount sufficient to block or interfere with cellular transport mechanisms that lead to pesticide resistance. Generally useful levels include a P-gp inhibitor within the range from about 5% to about 20%, preferably within the range from about 5% to about 10% by weight based on the entire applied formulation. Stated in another way, the ratio of pesticide to P-gp inhibitor is desirably within the range from about 95:5 to about 80:20 more preferably within the range from about 95:5 to about 90:10, based on the weights of each.

When used as a sequential treatment, target pest populations are treated with a P-gp inhibitor before contact with the pesticide. The inhibitor component can be applied 1–24 hours before contact with the pesticide followed by pesticide application at the recommended rate for the particular pesticide.

Pesticides useful for the invention are those effective to control the target populations by killing or sterilizing the target pest. Generally, pesticides are applied in the form of liquids or solids and usually in combination with an inert diluent or carrier to meet the application rate or treatment identified by the pesticide manufacturer for controlling the population of the target pest. Generally, compositions according to the invention contain pesticide in an amount within the range of 0.01–99 wt%, preferably 0.1–50 wt%, even more preferably an amount within the range of 0.01–25 wt% based on the total composition.

Pesticides useful in the invention are toxic to the target pest and can be the subject of a developed resistance by the target pest. Structural features characteristics of such a potential for development of resistance include at least one aromatic ring and a hydrophobic domain, or a nitrogen atom within the chemical structure.

Exemplary pesticides useful in compositions of the invention generally exhibit insecticidal activity and include solid and liquid forms of the carbamates (e.g., carbaryl, aldicarb, methomyl, carbofuran, bendiocarb, oxamyl, thiodicarb, trimethylcarb); organophosphates (e.g., phorate, terbufos, fonophos, isofenphos, ethoprop, fenamiphos, disulfoton, malathion, parathion, demeton, dimethoate, chlorpyrifos, diazinon, monocrotophos, sulprophos, temephos, and phosmet); compounds which break down a pest's digestive tract tissue including fluorine compounds (cryolite) and nicotine; rotenone; neem oil or azadiractin; natural or synthetic pyrethroids (e.g., permethrin, cypermethrin and deltamethrin); petroleum oils; and the halogenated hydrocarbons (e.g., endrin, aldrin and its epoxide, dieldrin, heptachlor, DDT, BHC, lindane, chlordane, methoxychlor, DDD, TDE, and the polychlorinated biphenyls). In general, organophosphates and the carbamates are preferred with chlorpyrifos, carbaryl and methomyl being most preferred.

Pest populations that can be treated by compositions according to the invention include insects (adult and larval forms), rodents, and any other pest that is treated with a pesticide and which may develop resistance thereto.

Pesticide formulations according to the present invention may contain one or more additional materials to assist in the handling, application, or effectiveness of the active pesticidal ingredient. Exemplary materials include any of the conventional diluents, solids, carriers, stickers, surfactants, viscosity adjusting agents, spreaders, gustatory stimulants, hydrating agents, diet, and the like.

Pesticide formulations according to the present invention can be applied as liquids, suspension, emulsions, or solids by conventional application techniques for each. The particular application method should follow the application rates suggested by the pesticide manufacturer for the particular pesticide and application method chosen. In general, the application rate of the pesticidally effective formulation of the present invention will deliver a quantity of pesticide sufficient to control the population of a target pest. With insects, the applied insecticide should be in a quantity sufficient to cause mortality or render the target insect sterile following consumption or contact. With rodents, the rodenticide should be applied in a quantity sufficient to kill or sterilize the rodent following consumption or contact.

The following examples are presented for purposes of illustration only and are not intended to limit the scope of the appended claims.

EXAMPLES

Example 1

The tobacco budworm (Heliothis virescens) has been reported as resistant to nearly every insecticide used against it including DDT, carbaryl, endrin, parathion, and monocrotophos. The P-gp levels in five strains of resistant and one strain of susceptible 3rd instar tobacco budworms were examined.

Tissues were dissected in 0.1M phosphate buffer (pH of 7.6) and placed into homogenization buffer containing 0.1M sodium phosphate (pH 7.6), 1 mM phenylthiourea, 1 mM dithiothreitol, and 1 mM EDTA. The tissues were homogenized and spun at 10,000 g for 10 minutes. The supernatant was filtered through glass wool and spun at 100,000 g for 1 hour. The final pellet was resuspended in microsomal storage buffer containing 0.1 mM sodium phosphate (pH 7.6), 0.1 mM phenylthiourea, 0.1 mM dithiothreitol, and 0.1 mM EDTA. The suspension was stored at $-70°$ C. until analyzed.

After determining the protein concentration, the samples were resolved on a 7.5% polyacrylamide gel by the method of Laemmli and transferred to nitrocellulose in a Tris/glycerine buffer containing 0.1% SDS and 20% methanol at low power overnight. The samples were incubated for 2 hours in a PBS blocking solution containing 2.5% nonfat dry milk and 0.1% Tween 20. The primary antibody, C219, was applied at 1 µg/ml and shaken for 8 hours at 4° C. The blot was washed with PBS. The secondary antibody, rabbit antimouse IgG, was applied at 100 µg/50 ml blocking solution and shaken for one hour at room temperature. After washing, the blot was incubated in $^{125}$I-protein A for one hour. The blot was washed in PBS and allowed to air dry. Autoradiography was used to visualize P-gp. The amount of P-gp protein present was quantified using densitometry.

The results show that resistant budworms have a 1.8 to 6.4 higher content of P-gp compared to the susceptible strain. The P-gp was localized primarily in the cuticle and fat body with little expression in the mid gut.

Example 2

Third instar, resistant tobacco budworms were administered 2 µl of quinidine (0.1 µg/g) every six hours for the day before treatment with the pesticide. One hour after the fourth administration of quinidine, one of two chlorpyrifos-acetone solutions were applied topically to insects pretreated with quinidine and to those not so treated. As shown in Table 1, mortality rates of 13% and 29% were seen after 24 hours for insects pretreated with quinidine. No mortality was seen for insects that did not receive quinidine.

TABLE 1

| Example | Pesticide | Conc. (µg/g) | Quinidine | Mortality Rate (%) |
|---|---|---|---|---|
| 2 | Chlorpyrifos (Topical) | 0.3 | no | 0 |
| | | 0.3 | yes | 13 |
| | | 3 | no | 0 |
| | | 3 | yes | 29 |

Example 3

Third instar tobacco budworms were given quinidine as in example 2 and topically treated with an aqueous solution containing either 3 or 33 µg/g of thiodicarb. Mortality after 24 hours was 25% and 49% for the quinidine-treated insects and either 0 or 20% mortality for insects topically treated with only the thiodicarb solution. See, Table 2.

TABLE 2

| Example | Pesticide | Conc. (µg/g) | Quinidine | Mortality Rate (%) |
|---|---|---|---|---|
| 3 | Thiodicarb (Topical) | 3 | no | 0 |
| | | 3 | yes | 25 |
| | | 33 | no | 25 |
| | | 33 | yes | 43 |

Example 4

Third instar, resistant tobacco budworms were administered 2 µl of quinidine (0.1 µg/g) every six hours for one day and then allowed to feed on cotton leaves dipped in thiodicarb solutions ranging from 25–200 ppm. Insects continued to be treated topically with quinidine every 12 hours following the first exposure to the cotton leaves and for the remainder of the experiment.

After 48 hours, a mortality of 10–60% was seen in insects receiving quinidine while those not receiving quinidine exhibited markedly lower mortality rates of 0–8%. See, Table 3. By itself, quinidine did not cause significant mortality.

TABLE 3

| Example | Pesticide | Conc. (ppm) | Quinidine | Mortality Rate (%) |
|---------|-----------|-------------|-----------|--------------------|
| 4 | Thiodicarb (oral) | 25 | no | 0 |
| | | 25 | yes | 10 |
| | | 50 | no | 0 |
| | | 50 | yes | 27 |
| | | 200 | no | 8 |
| | | 200 | yes | 60 |

We claim:

1. A pesticide composition for inhibiting the development of pesticide resistance in a target pest population, said composition comprising: (a) an insecticidally active ingredient in an amount sufficient to control a population of a target insect; and (b) an inhibitor for ATP-dependent 15–180 kDa membrane P-glycoprotein selected from the group consisting of a calcium channel blocker, a calmodulin antagonist, tamoxifen, quinine, quinidine, a protein kinase C inhibitor, and a cyclosporin in an amount sufficient to interfere with cellular transport mechanisms that lead to insecticide resistance in said target insect.

2. A pesticide composition according to claim 1 wherein said pesticidally active ingredient is a carbamate, organophosphate, natural or synthetic pyrethroid, or halogenated hydrocarbon.

3. A pesticide composition according to claim 1 wherein said pesticidally active ingredient is a carbamate.

4. A pesticide composition according to claim 1 wherein said pesticidally active ingredient is an organophosphate.

5. A pesticide composition for inhibiting the development of pesticide resistance, said composition comprising: (a) a pesticidally active ingredient in an amount sufficient to control a population of a target pest; and (b) an inhibitor for ATP-dependent 150–180 kDa membrane P-glycoprotein selected from the group consisting of calcium channel blockers.

6. A pesticide composition according to claim 1 wherein said inhibitor is a calcium channel blocker, quinine, or quinidine.

7. A pesticide composition according to claim 1 wherein said inhibitor is quinidine.

8. A method for inhibiting insecticide resistance by a process comprising:
   delivering to an area exhibiting a target insect population in a quantity sufficient to kill said target insect a pesticide composition comprising a pesticidally active ingredient and an inhibitor for ATP-dependent 150–180 kDa a membrane P-glycoprotein selected from the group consisting of a calcium channel blocker, a calmodulin antagonist, tamoxifen, quinine, quinidine, a protein kinase C inhibitor, and a cyclosporin in an amount sufficient to interfere with cellular transport mechanisms that lead to pesticide resistance in said target pest.

9. A method as in claim 8 wherein said process comprises:
   delivering to said area a pesticide composition comprising an organophosphate and an inhibitor for ATP-dependent 150–180 kDa membrane P-glycoprotein.

10. A method as in claim 8 wherein said process comprises:
    delivering a pesticide composition comprising a carbamate and an inhibitor for ATP-dependent 150–180 kDa membrane P-glycoprotein to said area.

11. A method as in claim 8 wherein said process comprises:
    delivering to said area in a quantity sufficient to kill said target insect a pesticide composition comprising a pesticidally active ingredient and an inhibitor for ATP-dependent 150–180 kDa membrane P-glycoprotein selected from the group consisting of calcium channel blockers, quinine, and quinidine.

12. A method as in claim 11 wherein said process comprises:
    delivering to said area a pesticide composition comprising quinine or quinidine.

13. A method for inhibiting the development of insecticide resistance by a process comprising:
    delivering to an area containing a target insect population an inhibitor for ATP-dependent 150–180 kDa membrane P-glycoprotein selected from the group consisting of calcium channel blockers, calmodulin antagonists, tamoxifen, quinine, quinidine, protein kinase C inhibitors, and cyclosporins in an amount sufficient to reduce insecticide resistance in said target insect population, and
    applying to said area a quantity of an insecticide sufficient to kill said target insect.

14. A method as in claim 13 wherein said process comprises:
    delivering to said area an organophosphate.

15. A method as in claim 13 wherein said process comprises:
    delivering a carbamate to said area.

16. A method as in claim 13 wherein said process comprises:
    delivering to said area an inhibitor for ATP-dependent 150–180 kDa membrane P-glycoprotein selected from the group consisting of calcium channel blockers, quinine, and quinidine.

17. A method as in claim 13 wherein said process comprises:
    delivering to said area an inhibitor comprising quinine or quinidine.

18. A method for inhibiting insecticide resistance by a process comprising:
    delivering to an area exhibiting a target insect population in a quantity sufficient to kill said target insect a pesticide composition comprising a pesticidally active ingredient and an inhibitor for ATP-dependent 150–180 kDa membrane P-glycoprotein selected from the group consisting of a calmodulin antagonist, verapamil, azidopine, nicardipine, nimodipine, tamoxifen, quinine, quinidine, a protein kinase C inhibitor, and a cyclosporin.

19. A method as in claim 18 wherein said process comprises:
    delivering to said area in a quantity sufficient to kill said target insect a pesticide composition comprising a pesticidally active ingredient and an inhibitor for ATP-dependent 150–180 kDa membrane P-glycoprotein selected from the group consisting of verapamil, azidopine, nicardipine, nimodipine, quinine, and quinidine.

20. A method for inhibiting the development of insecticide resistance by a process comprising:

delivering to an area containing a target insect population an inhibitor for ATP-dependent 150–180 membrane P-glycoprotein selected from the group consisting of verapamil, azidopine, nicardipine, nimodipine, tamoxifen, calmodulin antagonists, quinine, quinidine, protein kinase C inhibitors, and cyclosporins, and applying to said area a quantity of an insecticide sufficient to kill said target insect.

21. A method as in claim 20 wherein said process comprises: delivering to said area an inhibitor for ATP-dependent 150–180 kDa membrane P-glycoprotein selected from the group consisting of verapamil, azidopine, nicardipine, nimodipine, quinine, and quinidine.

* * * * *